United States Patent
Schmitz et al.

(10) Patent No.: US 8,891,731 B2
(45) Date of Patent: Nov. 18, 2014

(54) SYSTEM AND METHOD FOR CONTROLLING A PORTABLE X-RAY SYSTEM

(75) Inventors: Andrea Marie Schmitz, Niskayuna, NY (US); Gerald Bowden Wise, Clifton Park, NY (US); Michael Dermot Denvir, Albany, NY (US); Jeffrey Wayne Eberhard, Albany, NY (US)

(73) Assignee: General Electric Company, Niskayuna, NY (US)

( * ) Notice: Subject to any disclaimer, the term of this patent is extended or adjusted under 35 U.S.C. 154(b) by 844 days.

(21) Appl. No.: 13/095,658

(22) Filed: Apr. 27, 2011

(65) Prior Publication Data

US 2014/0112437 A1 Apr. 24, 2014

(51) Int. Cl.
*G01N 23/04* (2006.01)
*A61B 6/00* (2006.01)

(52) U.S. Cl.
CPC ... *A61B 6/54* (2013.01); *A61B 6/56* (2013.01); *A61B 6/4405* (2013.01); *A61B 6/548* (2013.01)
USPC ............................................. 378/62; 378/116

(58) Field of Classification Search
CPC ........ A61B 6/4405; A61B 6/548; A61B 6/54; A61B 6/56
USPC .......................................... 378/62, 114–116
See application file for complete search history.

(56) References Cited

U.S. PATENT DOCUMENTS

| | | | |
|---|---|---|---|
| 7,664,222 B2 | 2/2010 | Jabri et al. | |
| 7,684,544 B2 | 3/2010 | Wilson | |
| 2006/0008054 A1 | 1/2006 | Ohara | |
| 2006/0242094 A1 | 10/2006 | Tamakoshi | |
| 2009/0065703 A1 | 3/2009 | Jadrich et al. | |
| 2009/0129547 A1 | 5/2009 | Jabri et al. | |
| 2009/0130983 A1 | 5/2009 | Venturino et al. | |
| 2009/0201841 A1 | 8/2009 | Tachikawa | |
| 2010/0123083 A1 | 5/2010 | Petrick et al. | |
| 2010/0166143 A1* | 7/2010 | Sung et al. ...................... | 378/62 |
| 2011/0013220 A1 | 1/2011 | Sabol et al. | |

FOREIGN PATENT DOCUMENTS

WO    2009067189 A1    5/2009

OTHER PUBLICATIONS

Search Report and Written Opinion from corresponding EP Application No. 12155718.5-2319 dated Aug. 21, 2012.

* cited by examiner

*Primary Examiner* — Courtney Thomas
(74) *Attorney, Agent, or Firm* — Fletcher Yoder, P.C.

(57) ABSTRACT

The subject matter disclosed herein relates to patient imaging systems, and more specifically, to portable X-ray imaging systems. In a first embodiment, a patient imaging system is presented. The patient imaging system includes an X-ray source configured to emit X-rays and a wireless X-ray detector configured to detect the emitted X-rays and acquire patient image data. The patient imaging system also includes an acquisition control system configured to initialize and prepare the patient imaging system for X-ray emission and detection. The acquisition control system is also configured to receive the acquired patient image data from the X-ray detector, and to non-deterministically control the operation of the X-ray source and the wireless X-ray detector. The patient imaging system also includes one or more user interfaces configured to instruct the acquisition control system when a user is ready for the patient imaging system to initialize, to prepare for X-ray emission and detection, and to begin X-ray emission and detection.

20 Claims, 4 Drawing Sheets

SYSTEM AND METHOD FOR CONTROLLING A PORTABLE X-RAY SYSTEM

STATEMENT REGARDING FEDERALLY SPONSORED RESEARCH & DEVELOPMENT

This invention was made with Government support under contract number W81XWH-08-2-0185 (Phase I contract number W81XWH-07-2-0013) awarded by U.S. Army Medical Research and Materiel Command. The Government has certain rights in the invention.

BACKGROUND

The subject matter disclosed herein relates to patient imaging systems, and more specifically, to portable X-ray imaging systems.

In the field of medicine, doctors routinely desire to conduct patient imaging examinations in order to non-invasively assess the internal tissue of a patient. While patient imaging systems, such as an X-ray imaging system, are typically present in hospitals and doctor's offices, a patient must be able to travel to such a location to have the imaging performed. However, certain settings (e.g., rural locations, developing nations, military field hospitals, etc.) may require patient imaging systems that are portable so that they may be brought into the field. In addition to portability, these systems must also be robust to deal with environmental limitations and conditions during system transport and operation.

An important advent in the field is the appearance of wireless X-ray detectors. A wireless X-ray detector offers numerous advantages, including portability and simple setup. In a portable patient imaging system involving a wireless X-ray detector, one challenge is synchronizing the various activities of the imaging system over a potentially unreliable wireless communication link. For example, since patient imaging involves exposing a patient to radiation from a radiation source, it is important that this attenuated radiation be detected in an efficient fashion to maximize the effectiveness of the exam while minimizing the exposure of the patient to radiation. Therefore, it is important to be able to synchronize the operation of the radiation source and detector so that the radiation that has passed through the patient may be properly detected and not be unnecessarily wasted. However, the wireless communication link used by wireless X-ray detectors, like all wireless communication, is subject to noise and interference. Since the wireless communication link may, at times, suffer from throughput or latency issues, the communication link may be unavailable or delayed in delivering messages.

BRIEF DESCRIPTION

In a first embodiment, a patient imaging system is presented. The patient imaging system includes an X-ray source configured to emit X-rays and a wireless X-ray detector configured to detect the emitted X-rays and acquire patient image data. The patient imaging system also includes an acquisition control system configured to initialize and prepare the patient imaging system for X-ray emission and detection. The acquisition control system is also configured to receive the acquired patient image data from the X-ray detector, and to non-deterministically control the operation of the X-ray source and the wireless X-ray detector. The patient imaging system also includes one or more user interfaces configured to instruct the acquisition control system when a user is ready for the patient imaging system to initialize, to prepare for X-ray emission and detection, and to begin X-ray emission and detection.

In a second embodiment, a method of controlling a patient imaging system is presented. The method includes receiving instructions from a user to initiate a patient exam and sending to a wireless X-ray detector an initialization scrub script, an image acquisition script, and offset acquisition script that define parameters of the patient exam. The method also includes instructing the wireless X-ray detector to execute the initialization scrub script, receiving instructions from the user to prepare an X-ray source to emit X-rays, and instructing the X-ray source to prepare to emit X-rays. The method also includes receiving instructions from the user to begin emitting X-rays from the X-ray source, instructing the wireless X-ray detector to execute the image acquisition script, and receiving a message from the wireless X-ray detector indicating that it is beginning execution of the image acquisition script. The method also includes instructing to the X-ray source to emit X-rays while the wireless X-ray detector is executing the image acquisition script and instructing the wireless X-ray detector to execute the offset acquisition script while the X-ray source is not emitting X-rays.

In a third embodiment, a method of acquiring an X-ray image using an X-ray imaging system is presented. The method includes instructing an acquisition control system via a first user interface to prepare a wireless X-ray detector for a patient imaging exam, instructing the acquisition control system via a second user interface to prepare an X-ray source for radiation emission, and instructing the acquisition control system via the second user interface to activate the X-ray source to emit radiation once the wireless X-ray detector is prepared for acquisition and the X-ray source is prepared for emission.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique addresses the aforementioned synchronization problem using a system acquisition controller to exchange a series of messages between the components (e.g., source, detector, user interface, etc.) of the portable patient imaging system to synchronize their operations. As described herein, the system controller may, for example, ensure that the system as a whole is prepared for radiation exposure before the radiation source is activated, even if messages are lost or delayed due to the potential wireless communication complications (e.g. disconnection, high latency, etc). Therefore, as described herein, it is possible to control the various components of the system in a non-deterministic fashion, where the system acquisition controller may function using only limited information regarding the internal state of the source and detector.

Figure 1:
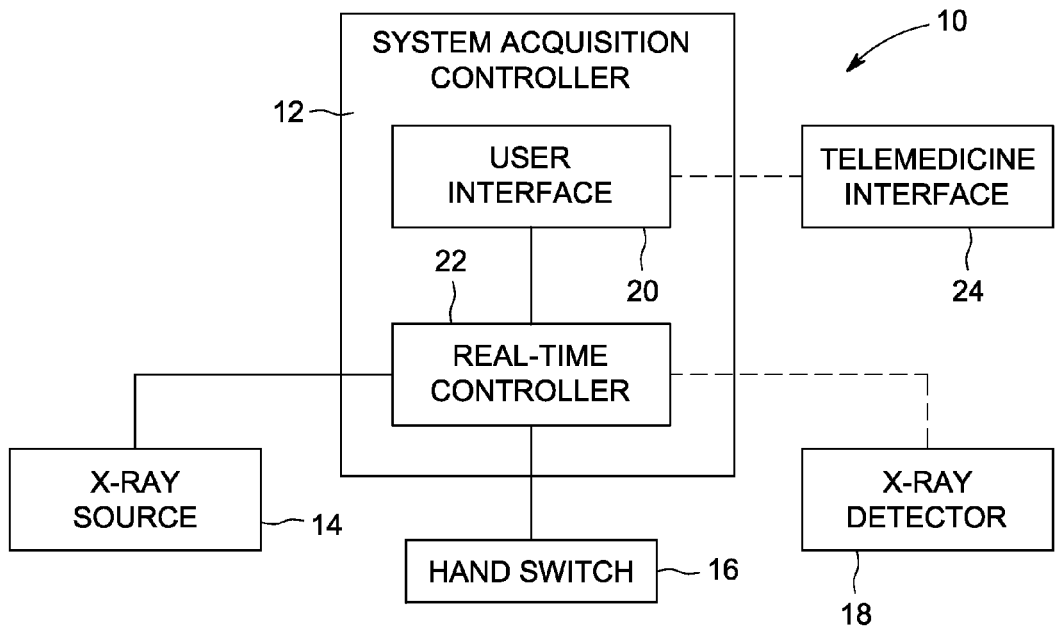
FIG. 1 is a block diagram illustrating an embodiment of a patient imaging system, in accordance with aspects of the present disclosure.

Turning to FIG. 1, an embodiment of a portable X-ray system 10 is presented. In such an embodiment, the system acquisition controller 12 is in communication with an X-ray source 14 and a hand switch 16 as well as wirelessly communicating with a wireless X-ray detector 18. In an embodiment, in order to maximize portability, the system acquisition controller 12 may be a laptop, notebook, tablet, or any such general purpose portable computing device. The X-ray source 14 may be an X-ray tube, a distributed X-ray source (such as a solid-state or thermionic X-ray source) or any other source of X-ray radiation suitable for the acquisition of medical or other images. The wireless X-ray detector may be a flat-panel wireless X-ray detector and may include an array of X-ray detection elements, memory, a processor, and a wireless communication interface.

The system acquisition controller 12 controls the operation of the portable X-ray system 10 and serves as a communication hub between the system components, as will be described in greater detail below. The system acquisition controller 12 includes a user interface 20 and a real-time controller 22. The user interface 20 may afford the operator the opportunity to enter information regarding that patient being imaged, make notes on the examination, set the parameters for the examination, etc. The real-time controller 22 is responsible for negotiating communications between the X-ray source 14, X-ray detector 18, hand switch 16, and user interface 20 in a dynamic and/or contemporaneous manner, as will be discussed in detail below. The system acquisition controller 12 is also responsible for receiving the acquired image and offset data wirelessly from the wireless X-ray detector so that the data may be processed into images. Additionally, the system acquisition controller 12 may be connected, physically or wirelessly, to a telemedicine interface 24 to allow the exchange of patient data with a remote data system such as via the Internet or a satellite data connection, or alternatively, using GSM, CDMA, or other similar wireless or cellular network. Specifically, the portable X-ray system 10 may use one of the aforementioned means of communication to exchange patient data with a picture archiving and communication system (i.e. PACS) so that others at different locations may gain access to the raw or processed image data.

Figure 2:
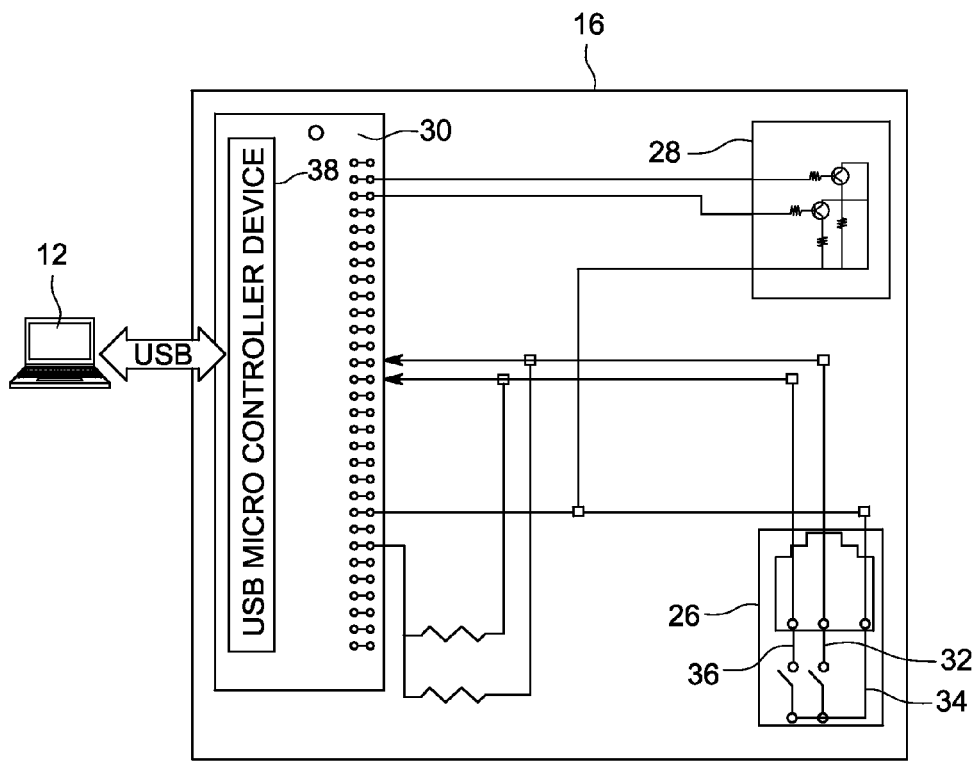
FIG. 2 is a circuit diagram illustrating an embodiment of a hand switch, in accordance with aspects of the present disclosure.

In an embodiment, the hand switch 16 is a hand-held controller that may be coupled to the system acquisition controller 12 using a universal serial bus (USB), as illustrated by the circuit diagram depicted in FIG. 2. As illustrated, the hand switch 16 may include a switch component 26, a comparison component 28, and a controller component 30. The switch component 26 may include a two-stage switch. When the operator selects a "Prepare" mode using the first stage of the switch, a first signal line 32 is connected to ground 34. When the operator selects "Emit" mode using the second stage of the switch, both the first 32 and second 36 signal lines may be connected to ground 34. The controller component 30 bridges the switch component 26 and the comparison component 28, which determines the state of the switch component 26 and sends either a "Prepare" or "Emit" signal back to the controller component 30, as appropriate. The controller component 30 also includes communication control circuitry (e.g., a USB microcontroller 38 or a serial microcontroller) configured to handle the communications between the hand switch 16 and the system acquisition controller 12. In an embodiment, the use of the ubiquitous USB standard interface may allow the hand switch 16 to be disconnected and connected to different system acquisition controllers 12 with ease.

Figure 3:
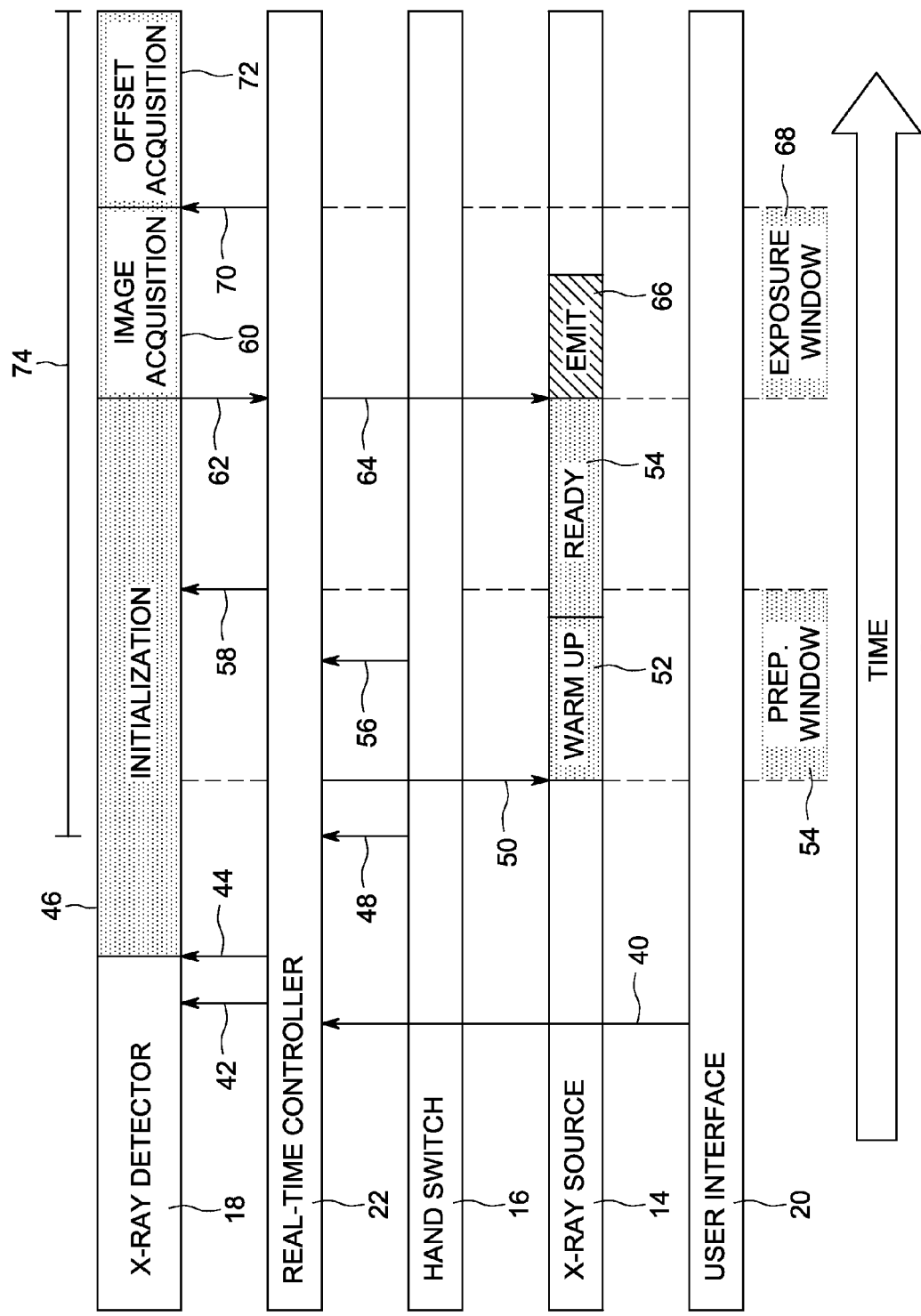
FIG. 3 illustrates an embodiment of the message exchange used to synchronize the activities of the components of the patient imaging system, in accordance with aspects of the present disclosure.

As mentioned above, the wireless communication link between the wireless X-ray detector 18 and the system acquisition controller 12 may suffer from reliability issues due to environmental interference or other factors. To overcome this potential problem, the real-time controller 22 of the system acquisition controller 12 orchestrates a series of message exchanges to coordinate the activities of the various system components relative to one another in time. For example, FIG. 3 presents an implementation that illustrates the exchange of messages between the components of the portable X-ray imaging system 10 during system operation. Specifically, FIG. 3 illustrates the communication between the wireless X-ray detector 18, real-time controller 22, hand switch 16, X-ray source 14, and the user interface 20 during a patient imaging examination. In the illustration, the vertical arrows extending between two components represent a message exchange between the two components at a relative point in time. It should be noted that since the message exchange between two components (e.g., the real-time controller 22 and the wireless X-ray detector 18) may take place using a standard networking protocol, such as a TCP, the message exchange may be divided into a series of packages for transmission and may also involve the transmission of one or more acknowledgment messages to confirm receipt of the original message.

The imaging process may begin with an initialization of the patient imaging system during which the operator may use the user interface 20 to enter the information about the patient. For example, the operator may enter a patient's name, age, gender, etc. into a graphical user interface. In some embodiments, the operator may only enter a minimal amount of information about the patient into the system, such as a serial number or a triage identifier. The operator may also use the user interface 20 to input the parameters of the patient examination (e.g., the region of the patient being imaged, the number of exposures, the length of the exposure, etc.) or to otherwise specify an imaging protocol. After entering the information, the operator may indicate to the user interface 20 that the examination may begin. In response, the user interface 20 sends a message 40 to the real-time controller 22 indicating that the operator is ready to begin the examination process.

After receiving the message 40 from the user interface 20 that the operator is ready to begin the exam, the real-time controller 22 sends a message 42 to the wireless X-ray detector 18 containing a series of instructions (i.e., scripts). More specifically, the real-time controller 22 sends the detector 18 three scripts: an initialization scrub script, an image acquisition script, and an offset acquisition script. In other implementations the scripts may be stored in memory on the detector 18 and the message 42 may simple cause a specified script to be loaded into memory. These scripts define the detector 18 parameters for the patient examination. For example, the scripts may control the length of time that the detector 18 will collect X-rays during image acquisition (i.e., detector exposure time). The scripts may also define number of times the detector 18 may acquire and discard data, commonly known as scrubbing, before and between image acquisitions as well as the length of time to wait between scrubbing cycles (i.e., scrubbing delay time).

After sending the message 42 containing or invoking the scripts, the real-time controller 22 sends another message 44 to the wireless X-ray detector 18 to instruct it to begin executing the scripts. The detector 18 responds by executing the initialization scrub script 46. When executing the initialization scrub script 46, the detector 20 is scrubbed at regular time intervals, allowing the electronics of the detector 20 to warm up and equilibrate. Repeatedly scrubbing the detector 18 may serve to warm up the electronic circuitry as well as prevent the detector 18 from accumulating and inadvertently incorporating noise data (e.g., data resulting from the detection of cosmic X-rays or electronic noise) into data collected during image or offset acquisition.

Figure 4:
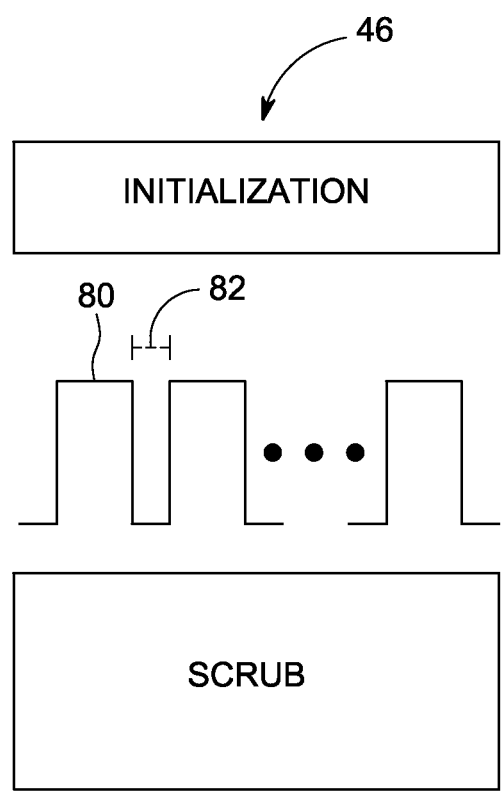
FIG. 4 illustrates the activities of a wireless X-ray detector when executing an embodiment of the initialization scrub script, in accordance with aspects of the present disclosure.
Figure 6:
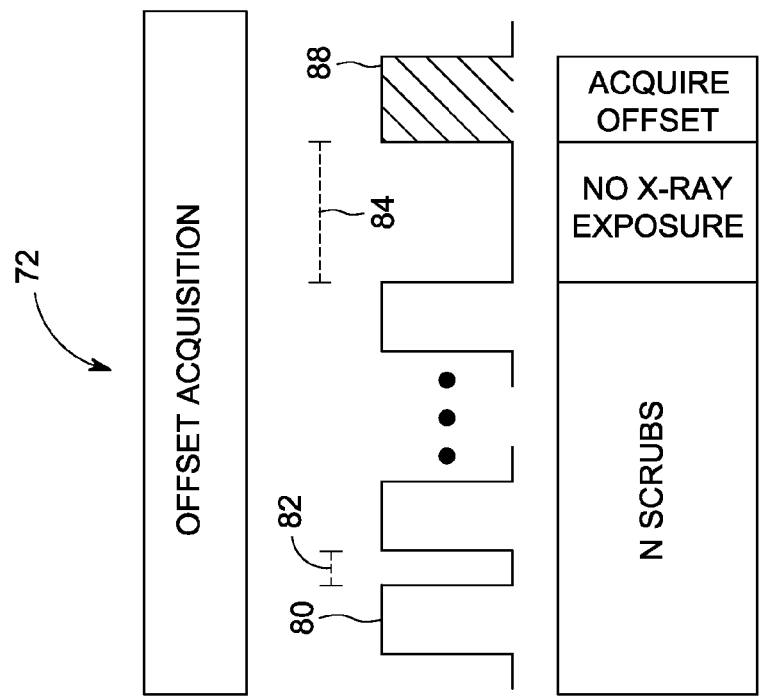
FIG. 6 illustrates the activities of a wireless X-ray detector when executing an embodiment of the offset acquisition script, in accordance with aspects of the present disclosure.

FIG. 4 depicts the behavior of a wireless X-ray detector 18 while executing an embodiment of the initialization scrub script. In FIG. 3, a number of square waves depict the scrubbing cycles of the detector 18, in which the peaks 80 represent the detector 18 acquiring an image that is immediately discarded. The regular interval between acquisitions is the scrubbing delay time 82, which, as mentioned above, is defined by the real-time controller 22 in the initialization scrub script 46. The detector 18 continues to execute the initialization scrub script 46, continually scrubbing until it is later signaled by the real-time controller 22 to stop.

Turning back to FIG. 3, while the wireless X-ray detector 18 is executing the initialization scrub script 46, the operator may, for example, position the patient, the X-ray detector 18, and the X-ray source 14 for a particular patient image. Once these have been positioned, the operator may select the "Prepare" mode using the hand switch 16, which then sends a message 48 to the real-time controller 22 indicating that the system 10 is to prepare for exposure and image acquisition. Accordingly, the real-time controller 22, after having received the message 48 from the hand switch 16, sends a message 50 to the X-ray source 14 to prepare for emission (i.e., warm up 52). This message 50 signifies the beginning of the preparation window 54, which is a period defined by the maximum amount of time for the X-ray source 14 to completely warm up 52 and be ready 54 for stable X-ray emission. As depicted in the illustration, while the X-ray source 14 may actually be ready 54 for emission at an earlier time, the real-time controller 22, lacking deterministic information about the state of the X-ray source 14, will not assume that the X-ray source 14 is ready to for emission before the preparation window 54 is over.

At some point after the operator has selected the "Prepare" mode using the hand switch 16, the operator may select the "Emit" mode, causing the hand switch 16 to send a message 56 to the real-time controller 22 that the patient is ready to begin exposure and image acquisition. However, the operator need not be aware of the status of the X-ray source 14 before selecting the "Emit" mode on the hand switch 16. As illustrated, the operator may even select the "Emit" mode during the preparation window 54, during which the X-ray source 14 may not be ready. As such, the real-time controller 22 will wait until the end of the preparation window 54 before proceeding to the next step.

After the real-time controller 22 has received the message 56 that the operator has selected the "Emit" mode using the hand switch 16, and after the preparation window 54 is completed, the real-time controller 22 sends a message 58 to the wireless X-ray detector 18 to instruct it to begin executing the image acquisition script 60. Before doing so, the initialization scrub script 46 may instruct the detector 18 to send a message 62 to the real-time controller 22 to indicate that it is about to begin executing the image acquisition script 60, and the detector 18 may not proceed with executing the image acquisition script until the message 62 is received by the real-time controller 22.

After the message 62 has been successfully exchanged, the detector 18 begins execution of the image acquisition script 60, which instructs the detector 18 to perform a specified number of scrubbing cycles before acquiring an image with a specified detector exposure time. FIG. 4 illustrates the activities of the wireless X-ray detector 18 while executing an embodiment of the image acquisition script 60. Similar to FIG. 3, FIG. 4 depicts a square wave in which the peaks 80 represent data acquisition. The detector 18 first completes a series of N scrubbing cycles, in which the number, N, as well as the scrubbing delay time 82, are defined by the real-time controller 22 in the image acquisition script 60. After completing N scrubbing cycles, the detector 18 collects X-rays for the extent of the detector exposure time 84, which is also defined by the real-time controller 22 in the image acquisition script 60. Finally, the detector acquires 86 the image data, which is stored in memory for later transmission to the system acquisition controller.

Turning again to FIG. 3, the real-time controller, having received the message 62 that the detector is about to begin execution of the image acquisition script 60, sends a message 64 to the X-ray source 14 that is waiting (i.e., in a ready state 54) to emit 66 X-rays. Sending of this message 64 to the X-ray source 14 marks the beginning of the exposure window 68, which is a period defined by the maximum length of time that the X-ray source 14 may emit 66 X-rays. As illustrated, the X-ray source 14 may emit 66 X-rays for only a portion of the exposure window 68. In other implementations, the X-ray source 14 may emit for the entire exposure window.

At the end of the exposure window 68, the real-time controller 22 may send a message 70 to the wireless X-ray detector 18 instructing it to execute the offset acquisition script 72. In other embodiments, the detector 18 may instead wait an amount of time after completing the image acquisition script 60 (i.e., until outside of the exposure window 68) before executing the offset acquisition script 72. In certain embodiments, after completion of the image acquisition script 60, the detector 18 may automatically resume execution of the initialization scrub script 46 (i.e., repeated scrubbing cycles as illustrated in FIG. 4) until message 70 is received from the real-time controller 22. For example, after completing the image acquisition script 60, the real-time controller 22 may allow the detector 18 to execute the initialization scrub script 46 until the detector 18 has transmitted the acquired image data to the real-time controller 22, at which time the real-time controller 22 may send the message 70 to the detector 18 to begin execution of the offset acquisition script 72.

The purpose of the offset acquisition script 72 is the acquisition of an offset image, also known as a dark image, which is an image acquired by the detector 18 when the X-ray source 14 is not emitting X-rays. The offset image may be subtracted from an acquired patient image (i.e. the image acquired when the X-ray source is emitting X-rays) in order to subtract out background noise inherent to the detector and/or the local environment. As such, the detector exposure time 84 for the acquisition of an offset image typically matches the detector exposure time 84 for the patient image acquisition, albeit without intentionally exposing the detector to X-rays.

Figure 5:
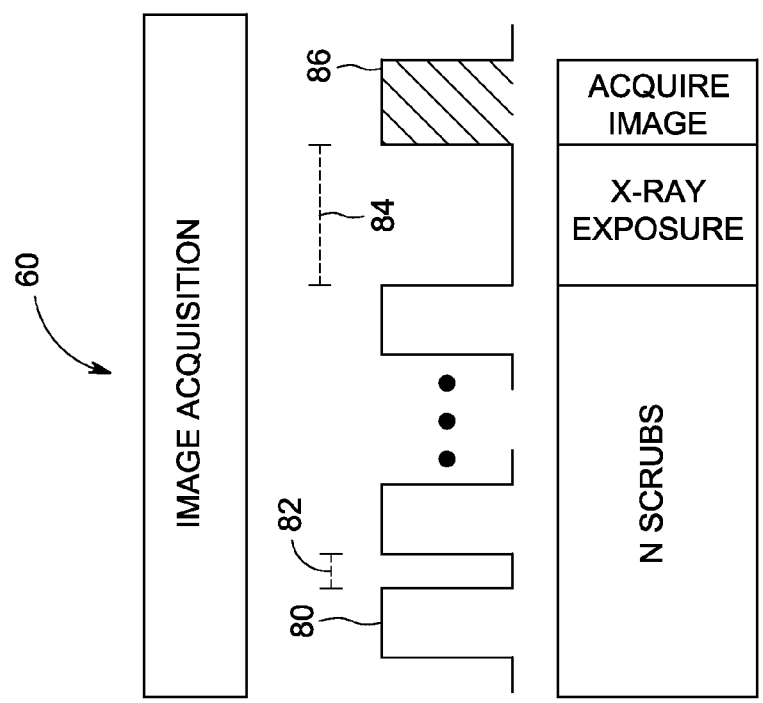
FIG. 5 illustrates the activities of a wireless X-ray detector when executing an embodiment of the image acquisition script, in accordance with aspects of the present disclosure.

FIG. 5 illustrates the activities of the wireless X-ray detector 18 while executing an embodiment of the offset acquisition script 72. Similar to FIGS. 3-4, FIG. 5 depicts a square wave in which the peaks 80 represent data acquisition. As with the execution of the image acquisition script 60, during execution of the offset acquisition script 72 the detector 18 first completes a series of N scrubbing cycles. The number, N, and the scrubbing delay time 82, are defined by the real-time controller 22 in the offset acquisition script 72. After completing N scrubbing cycles, the detector 18 collects X-rays for the detector exposure time 84, even though X-rays are not being emitted by the X-ray source 14. As mentioned above, the detector exposure time 84 for the offset acquisition script 72 is typically the same as the detector exposure time 84 for the image acquisition script 60. Finally, the detector acquires 88 the offset image data, which is stored for later transmission to the system acquisition controller 12.

In an embodiment, the operator may repeatedly select the "Prepare" and "Emit" modes using the hand switch for each subsequent image/offset acquisition. Between each image/offset acquisition, the detector 18 may execute the initialization scrub script 46 until the real-time controller 22 sends the message 58 to the detector, indicating that the "Prepare" and "Emit" modes have been selected in series and that the preparation window is complete. Accordingly, the indicated portion 74 identifies the portion of FIG. 3 that would be repeated for subsequent image acquisition for such an embodiment. Additionally, the image and offset data acquired may be stored in the memory of the detector until the completion of each image acquisition (i.e., X-ray image and associated offsets), after which, the wireless detector may transfer the data to the system acquisition controller 12 for further processing.

In the embodiment demonstrated in FIG. 3, there are a series of safe-guards that may be implemented in the design of the real-time controller 22 to ensure that certain conditions have been met before proceeding with the next step in the process. For example, before the user interface 20 sends the message 40 to the real-time controller 22 indicating that the operator is ready to begin the exam, selecting the "Prepare" or "Emit" modes using the hand switch 16 will be ignored by the system 10. Likewise, as previously mentioned, the real-time controller 22 will not send the message 58 to the wireless X-ray detector 18 to begin executing the imaging acquisition script 60 until the all of the following conditions have been met: "Prepare" mode has been selected using the hand switch 16, "Emit" mode has been selected using the hand switch 16, and the preparation window 54 is completed. Also, the real-time controller 22 will not send the message 64 to the X-ray source 14 to emit 66 X-rays until all of the following conditions have been met: the "Prepare" and "Emit" modes have been selected, the preparation window 54 is complete, and the detector 18 has already sent the message 62 indicating that it is beginning to execute the image acquisition script 60.

Furthermore, the safe-guards described above as well as the sequence of message exchanges between the real-time controller 22 and the wireless X-ray detector 18 ensure that the emission only takes place when the detector 18 is executing the image acquisition script 60, regardless of the stability of the wireless network. For example, if the wireless X-ray detector 18 becomes disconnected from the real-time controller 22 before exchanging the message 62 (indicating that the detector 18 is about to begin the image acquisition script 60) the real-time controller 22 will wait for the message 62 before proceeding, potentially allowing the detector adequate time to wirelessly reconnect to the real-time controller 22. In another example, the wireless communication link between the real-time controller 22 and the detector 18 may suffer from a high latency due to environmental noise, delaying the delivery of message 62 from the detector 18 to the real-time controller 22 and/or delaying the delivery of the associated acknowledgment message from the real-time controller 22 to the detector 18 indicating that message 62 has been received by the real-time controller. By requiring that message 62 is both successfully delivered and acknowledged before either the real-time controller 22 or the detector 18 proceed, the actions of both may be effectively synchronized.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A patient imaging system, comprising:
an X-ray source configured to emit X-rays;
a wireless X-ray detector configured to detect the emitted X-rays and acquire patient image data; and
a controller configured to:
receive a plurality of inputs related to a patient imaging exam from a first user interface, and, in response, generate a plurality of control scripts for the patient imaging exam based on the plurality of inputs;
send the plurality of control scripts to the wireless X-ray detector for execution, wherein the plurality of control scripts comprise an initialization scrub script and an image acquisition script; and
send an initialization signal to the wireless X-ray detector to cause the wireless X-ray detector to begin execution of the initialization scrub script before executing the image acquisition script.

2. The patient imaging system of claim 1, wherein the first user interface is a graphical user interface (GUI) of a computer that is configured to receive the plurality of inputs related to the patient imaging exam from a user, and provide the plurality of inputs to the controller.

3. The patient imaging system of claim 1, wherein the controller is configured to:
receive a first input from a second user interface requesting preparation of the patient imaging system, and, in response, send a warm-up signal to the X-ray source to cause the X-ray source to begin warming up;
receive a second input from the second user interface requesting image acquisition, and, in response, send an image acquisition signal to the wireless X-ray detector to cause the wireless X-ray detector to begin executing the image acquisition script after a preparation time window has passed; and
receive an acquiring image signal from the wireless X-ray detector when the wireless X-ray detector begins execution of the image acquisition script and, in response, send an emit signal to the X-ray source to cause the X-ray source to emit X-rays during an exposure time window.

4. The patient imaging system of claim 3, wherein the second user interface is a two-stage switch comprising a first stage that provides the first input when activated by a user and a second stage that provides the second input when activated by the user.

5. The patient imaging system of claim 3, wherein the wireless X-ray detector is configured to:
receive the plurality of control scripts from the controller;

receive the initialization signal from the controller, and in response, execute the initialization scrub script; and receive the image acquisition signal from the controller, and in response, execute the image acquisition script after the preparation time window has passed.

6. The patient imaging system of claim 5, wherein the plurality of control scripts comprise an offset acquisition script, wherein the controller is configured to send an offset acquisition signal to the wireless X-ray detector to cause the wireless X-ray detector to begin execution of the offset acquisition script after the exposure time window is complete, and wherein the wireless X-ray detector is configured to receive the offset acquisition signal and, in response, execute the offset acquisition script to obtain at least one dark image.

7. The patient imaging system of claim 6, wherein the wireless X-ray detector is configured to execute the initialization scrub script again after completing execution of the offset acquisition script, and provide the image acquisition signal to the wireless X-ray detector after the first input is again received from the second user interface.

8. A method of controlling an X-ray patient imaging system, comprising:

receiving a first input requesting initiation of a patient exam;

sending to a wireless X-ray detector an initialization scrub script, an image acquisition script, and an offset acquisition script that define parameters of the patient exam;

instructing the wireless X-ray detector to execute the initialization scrub script;

receiving a second input requesting preparation of an X-ray source to emit X-rays;

instructing the X-ray source to prepare to emit X-rays during a preparation time window;

receiving a third input requesting emission of X-rays from the X-ray source;

instructing the wireless X-ray detector to execute the image acquisition script after the preparation time window has passed;

receiving a message from the wireless X-ray detector indicating that the wireless X-ray detector is beginning execution of the image acquisition script;

instructing the X-ray source to emit X-rays while the wireless X-ray detector is executing the image acquisition script; and instructing the wireless X-ray detector to execute the offset acquisition script while the X-ray source is not emitting X-rays.

9. The method of claim 8, comprising receiving at least one image and at least one offset image acquired by the wireless X-ray detector.

10. The method of claim 8, wherein receiving the first input requesting initiation of the patient exam comprises receiving patient data and patient exam parameters from a graphical user interface.

11. The method of claim 8, wherein the second and third inputs are received from a hand switch user interface.

12. The method of claim 8, comprising sending a confirmation message to the wireless X-ray detector to confirm receipt of the message from the wireless X-ray detector before instructing the X-ray source to emit X-rays.

13. The method of claim 8, wherein instructing the X-ray source to emit X-rays comprises instructing the X-ray source to emit X-rays during an exposure time window; and wherein instructing the wireless X-ray detector to execute the offset acquisition script comprises instructing the wireless X-ray detector to execute the offset acquisition script after the exposure time window has passed.

14. The method of claim 10, wherein the initialization scrub script, the image acquisition script, and the offset acquisition script define parameters of the patient exam based on the patient data and patient exam parameters received from the graphical user interface.

15. A method of acquiring an X-ray image, comprising:

receiving a first input from a graphical user interface requesting initialization of a wireless X-ray detector for a patient imaging exam, wherein the first input comprises parameters for the patient imaging exam;

receiving a second input from a two-stage switch user interface requesting preparation of an X-ray source for radiation emission; and receiving a third input from the two-stage switch user interface requesting activation of the X-ray source to emit radiation; and signaling the X-ray source to activate and emit radiation only after both receiving the third input and receiving a message indicating that the wireless X-ray detector has completed initialization and is executing an image acquisition script to acquire the X-ray image.

16. The method of claim 15, comprising providing an initialization scrub script and the image acquisition script to the wireless X-ray detector in response to receiving the first input from the graphical user interface.

17. The method of claim 16, comprising signaling the wireless X-ray detector to execute the initialization scrub script in response to receiving the first input from the graphical user interface.

18. The method of claim 15, comprising signaling the X-ray source to prepare for radiation emission in response to receiving the second input from the from the two-stage switch user interface, wherein the X-ray source is ready to emit radiation when a preparation time window has passed after signaling the X-ray source to prepare for radiation emission.

19. The method of claim 18, comprising signaling the wireless X-ray detector to execute the image acquisition script after receiving the third input from the two-stage switch user interface and after the preparation time window has passed.

20. The method of claim 15, comprising signaling the wireless X-ray detector to execute an offset acquisition script when an exposure time window has passed after receiving the message from the wireless X-ray indicating that the wireless X-ray detector is executing an image acquisition script.

* * * * *